(12) United States Patent
Lesho et al.

(10) Patent No.: US 6,553,244 B2
(45) Date of Patent: Apr. 22, 2003

(54) ANALYTE MONITORING DEVICE ALARM AUGMENTATION SYSTEM

(75) Inventors: Matthew J. Lesho, San Mateo, CA (US); Samuel A. Morley, Jr., Richmond, CA (US)

(73) Assignee: Cygnus, Inc., Redwood City, CA (US)

(*) Notice: Subject to any disclaimer, the term of this patent is extended or adjusted under 35 U.S.C. 154(b) by 0 days.

(21) Appl. No.: 09/927,575

(22) Filed: Aug. 10, 2001

(65) Prior Publication Data

US 2002/0065453 A1 May 30, 2002

Related U.S. Application Data

(60) Provisional application No. 60/226,133, filed on Aug. 18, 2000.

(51) Int. Cl.⁷ ................................................. A61B 5/05
(52) U.S. Cl. ........................ 600/347; 600/300; 600/345; 600/365
(58) Field of Search ........................... 600/300–301, 600/345–347, 365

(56) References Cited

U.S. PATENT DOCUMENTS

| | | | | |
|---|---|---|---|---|
| 5,140,985 A | * | 8/1992 | Schroeder et al. | 600/323 |
| 5,507,288 A | * | 4/1996 | Böcker et al. | 600/322 |
| 5,807,375 A | * | 9/1998 | Gross et al. | 604/890.1 |
| 6,134,461 A | * | 10/2000 | Say et al. | 600/345 |
| 6,144,869 A | * | 11/2000 | Berner et al. | 600/347 |
| 6,159,147 A | * | 12/2000 | Lichter et al. | 600/300 |
| 6,175,752 B1 | * | 1/2001 | Say et al. | 600/345 |

OTHER PUBLICATIONS

Bolinder et al., "Self–Monitoring of Blood Glucose in Type I Diabetic Patients: Comparison with Continuous Microdialysis Measurements of Glucose In Subcutaneous Adipose Tissue During Ordinary Life Conditions," *Diabetes Care* 20(1):64–70 (1997).

Ohkubo et al., "Intensive Insulin Therapy Prevents the Progression of Diabetic Microvascular Complications in Japanese patients with Non–Insulin–Dependent Diabetes Mellitus: a Randomized Prospective 6–year Study," *Diabetes Research & Clinical Practice* 28:103–117 (1995).

UK Prospective Diabetes Study (UKPDS) Group., "Effect of Intensive Blood–Glucose Control With Metformin on Complications in Overweight Patients with Type 2 Diabetes (UKPDS 34)," *Lancet* 352:837–853 (1998).

* cited by examiner

*Primary Examiner*—Max F. Hindenburg
*Assistant Examiner*—Patricia Mallari
(74) *Attorney, Agent, or Firm*—Barbara G. McClung; Gary R. Fabian (57) ABSTRACT

The present invention relates to a device for augmenting an alarm signal generated by an analyte monitoring device, e.g., the GlucoWatch® (Cygnus, Inc., Redwood City, Calif.) biographer glucose monitoring device, for improving the alarm signal's effectiveness in alerting the user, and/or for communicating the signal to a person or person(s) other than the user, or to a trained assistance animal.

20 Claims, 1 Drawing Sheet

FIG. 1

ANALYTE MONITORING DEVICE ALARM AUGMENTATION SYSTEM

CROSS-REFERENCE TO RELATED APPLICATIONS

This application is related to U.S. Provisional Patent Application Serial No. 60/226,133, filed Aug. 18, 2000, from which priority is claimed under 35 USC §119(e)(1), and which application is incorporated herein by reference in its entirety.

TECHNICAL FIELD

The present invention generally relates to a system for augmenting an alarm signal from an analyte monitoring device, e.g., the GlucoWatch® (Cygnus, Inc., Redwood City, Calif.) biographer glucose monitoring device.

An exemplary device for use with the present invention is the GlucoWatch biographer, a device which monitors glucose levels in an individual user and generates an aural alert signal upon sensing glucose levels outside of a predetermined range, thereby alerting the user that he or she is hypo- or hyper-glycemic, and that corrective action is necessary. Further, the device sounds an alert if glucose levels are falling too rapidly. The device comprises two primary elements, a durable element (comprising a watch-type housing, display element, microprocessor element, electrical connector elements, and may further comprise a power supply) and a consumable element (e.g., an AutoSensor component involved in sampling and signal detection).

In some cases, however, an aural signal provided by an analyte monitoring device may be inadequate to alert an individual user of an analyte monitoring device that the analyte amount or concentration is not within the normal predetermined range. For example, the user may be asleep or physically impaired. Alternately, the user may be a small child or animal who is unable to take the action required, e.g., administering glucose, insulin, or alerting an adult who may provide assistance. In a worst-case scenario, the detected analyte abnormality may render the user incapable of perceiving the signal or of seeking help, such as in the case of insulin shock or diabetic coma.

In such cases, augmentation and/or transmission of the alarm signal to another person or to emergency personnel is desirable.

However, until now, an alarm augmentation system for an analyte monitoring device, e.g., the GlucoWatch biographer, has not been described or suggested.

SUMMARY OF THE INVENTION

The present invention relates to an augmented alarm system for use with an analyte monitoring device.

In a first aspect of the invention, the augmented alarm system constitutes an improvement to a pre-existing analyte monitoring device (for example, a glucose monitoring device) that provides an alert or alarm, e.g., when analyte values (or predicted analyte values) fall outside of a predetermined range. The improvement results from modification of the device's circuitry which renders the device capable of producing a auditory, visual, tactile (or kinesthetic), olfactory, or gustatory stimulus, or variations or combinations thereof. That stimulus serves as the augmented alarm signal.

In one embodiment of this first aspect of the invention, the analyte monitoring device is the GlucoWatch biographer. Typically modification of the device's system comprises changes to the durable element of the system, although the consumable component of the Glucowatch biographer (i.e., the AutoSensor) may also be modified. For example, the iontophoretic channels of the monitoring device's durable element are modified to deliver an electrical current, typically delivered through the ionically conductive material of the consumable element, so as to provide a tactile stimulus that serves as the augmented alarm signal.

In a second aspect of the invention, the augmented alarm system constitutes an improvement to a pre-existing analyte monitoring system, for example, a glucose monitoring device. In this second aspect of the invention, the improvement results from modification of the device's circuitry, typically of the durable element, to provide a connection to a first and/or second signaling component for producing alarm signals to alert a user of the monitoring device (or to alert others) to analyte levels outside of a predetermined range.

In one embodiment of this second aspect of the invention, the analyte monitoring device is the GlucoWatch biographer glucose monitoring device. Some modifications to provide a connection to a first and/or second signaling component include, but are not limited to, modifications to the following elements of the durable component: reconfiguring the confidence loop of the analyte monitoring device, modifying the transmission and receipt lines, modifying the sweat probes, or adding a serial port, which is placed in operative communication with the analyte monitoring device. In one aspect, the connection may be via a wire-like connector or alternately, via a telemetering system. The telemetering system may take a variety of forms, including but not limited to, electromagnetic radiation, capacitance coupling, inductive coupling, infrared coupling, and may further include variations and combinations thereof. In yet another embodiment, the first signaling component may be an auditory stimulus generator, a visual stimulus generator, a tactile stimulus generator (including but not limited to a kinesthetic stimulus generator), an olfactory stimulus generator, a gustatory stimulus generator, or variations or combinations thereof.

In a third aspect of the invention, the augmented alarm system may be an integral part of an analyte monitoring device, for example, a glucose monitoring device. The analyte monitoring device may comprise (a) an acquisition unit capable of at least sensing or detecting analyte concentrations or amounts in a subject; (b) a display unit, operably linked to said acquisition unit, wherein (i) the display unit comprises means to provide an audible alert when an analyte level, in a subject being monitored, is outside of a predetermined range, and (ii) the acquisition unit and the display units are separately housed; and (c) an alarm augmentation system comprising a first signaling component, capable of producing alarm signals to alert a subject in response to analyte levels outside of a predetermined range. The first signaling component is typically operably linked to the display unit. In this embodiment the acquisition unit and the display unit, each operably connected to the other, are typically separately housed. The augmented alarm system may be housed with the display unit, or separately housed as well. In one embodiment, the display unit comprises at least a first signaling component, operably connected to the display unit, for producing augmented alarm signals to alert a user in response to analyte levels outside of a predetermined range.

In one embodiment of this third aspect of the invention, the first signaling component is a stimulus generator capable of generating auditory, visual, tactile (including but not limited to kinesthetic), olfactory or gustatory stimuli, or variations or combinations thereof. In one exemplary embodiment, the first signaling component is an auditory stimulus generator which provides a volume control for varying the volume of auditory stimuli.

In another embodiment of this third aspect, the display unit further includes a transmitter component that is operably linked to the display unit, for transmitting alarm signals to at least one external communication target; it may also provide an operative link between the display unit and the first signaling component. The transmitter component may take the form of a serial port and a wire-like connector, the port being capable of connecting with one or more external communication targets; alternately, the transmitter component may be a telemetering system. A variety of possible telemetering systems may be employed, which include but are not limited to electromagnetic radiation, capacitance coupling, inductive coupling, infrared coupling, and may further include variations or combinations thereof.

In yet another embodiment of the third aspect of the invention, the telemetering system may be capable of connecting with other alarm augmentation system components, including but not limited to first and/or second signaling components.

In still another embodiment, the analyte monitoring device with alarm augmentation system may further include a second signaling component, for example, operably linked to the transmitter component via a telemetering system, for producing alarm signals to alert a person or persons other than the user of the analyte monitoring device to analyte levels outside of a predetermined range. The second signaling component may be an auditory, visual, tactile (including, but not limited to kinesthetic), olfactory, or gustatory stimulus generator, or variations or combinations thereof.

In a further embodiment of the third aspect of the invention, the analyte monitoring device may further include a processor component, which is operably linked to the acquisition unit, the display unit, the transmitter component, and the first and second signaling components. The processor component may be capable of receiving and processing information received from the acquisition unit and the first and second signaling components, and may further be capable of controlling the operation of the transmitter component as well as the first and second signaling components.

These and other embodiments of the present invention will readily occur to those of ordinary skill in the art in view of the disclosure herein.

DESCRIPTION OF THE INVENTION

All publications, patents and patent applications cited herein are hereby incorporated by reference in their entireties.

1. Definitions

It is to be understood that the terminology used herein is for the purpose of describing particular embodiments only, and is not intended to be limiting. As used in this specification and the appended claims, the singular forms "a", "an" and "the" include plural referents unless the context clearly dictates otherwise. Thus, for example, reference to "a reservoir" includes a combination of two or more such reservoirs, reference to "an analyte" includes mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published Sep. 5, 1991; U.S. Pat. No. 5,636,632), suction, electroporation, thermal poration, passive diffusion (see, e.g., International Publication Nos.: WO 97/38126 (published Oct. 16, 1997); WO 97/42888, WO 97/42886, WO 97/42885, and WO 97/42882 (all published Nov. 20 1997); and WO 97/43962 (published Nov. 27, 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; International Publication WO 99/44507, published Sep. 10, 1999; International Publication WO 99/44638, published Sep. 10, 1999; and International Publication WO 99/40848, published Aug. 19, 1999). Iontophoretic sampling devices are described, for example, in International Publication No. WO 97/24059, published Jul. 10, 1997; European Patent Application EP 0942 278, published Sep. 15, 1999; International Publication No. WO 96/00110, published Jan. 4, 1996; International Publication No. WO 97/10499, published Mar. 2, 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" or "analyte monitoring device" refer to a system useful for obtaining frequent measurements of a physiological analyte present in a biological system. Such a device is useful, for example, for monitoring the amount or concentration of an analyte in a subject. Such a system may comprise, but is not limited to, a sampling mechanism, a sensing mechanism, and a microprocessor mechanism in operative communication with the sampling mechanism and the sensing mechanism. Such a device typically provides frequent measurement or determination of analyte amount or concentration in the subject and provides an alert or alerts when levels of the analyte being monitored fall outside of a predetermined range. Such devices may comprise durable and consumable (or disposable) elements. The term "glucose monitoring device" refers to a device for monitoring the amount or concentration of glucose in a subject. Such a device typically provides a frequent measurement or determination of glucose amount or concentration in the subject and provides an alert or alerts when glucose levels fall outside of a predetermined range. One such exemplary glucose monitoring device is the GlucoWatch biographer available from Cygnus, Inc., Redwood City, Calif., U.S. The GlucoWatch biographer comprises two primary elements, a durable element (comprising a watch-type housing, circuitry, display element, microprocessor element, electrical connector elements, and may further comprise a power supply) and a consumable, or disposable, element (e.g., an AutoSensor component involved in sampling and signal detection, see, for example, WO 99/58190, published Nov. 18, 1999). This and similar devices is described, for example, in the following publications: Tamada, et al., (1999) JAMA 282:1839–1844; U.S. Pat. No. 5,771,890, issued Jun. 30, 1998; U.S. Pat. No. 5, 735,273, issued Apr. 7, 1998; U.S. Pat. No. 5,827,183, issued Oct. 27, 1998; U.S. Pat. No. 5,954,685, issued Sep. 21, 1999; U.S. Pat. No. 5,989,409, issued Nov. 23, 1999; U.S. Pat. No. 6,023,629, issued Feb. 8, 2000; EP Patent Application EP 0 942 278 A2, published Sep. 15, 1999; PCT International Application WO 96/001 100, published Jan. 4, 1996; PCT International Application WO 99/5 8190, published Nov. 18, 1999. The GlucoWatch biographer provides a device for frequent sampling of glucose from a subject the application of low intensity electric fields across the skin (iontophoresis) to enhance the transport of glucose from body tissues to a sampling chamber. In addition, when the concentration or amount of glucose has been determined to be outside of a predetermined range of values the GlucoWatch biographer produces an alert or alarm signal. Such an alert or alarm is a component of the GlucoWatch biographer.

In a further embodiment, the analyte monitoring device of the present invention may comprise an "acquisition unit" and a "display unit." An "acquisition unit" is a device that is capable of at least sensing or detecting analyte concentrations or amounts (e.g., a sensing device, or an analyte monitoring device comprising sampling and sensing devices) and of transmitting that data to a "display unit." In turn, a "display unit" is a device capable of receiving data from an acquisition unit and exhibiting that data using, e.g., an LCD screen. The acquisition unit and display unit may be contained together in a single housing, or separately housed.

The terms "alarm augmentation system," and "alarm system" are used interchangeably herein, and refer to the analyte monitoring device alarm augmentation system that is the subject of the present invention, for example, the GlucoWatch biographer provides an alert to the user and a glucose monitoring device alarm augmentation system may be used to provide an enhanced alarm as described herein.

A "component" is a conceptual part of the entire alarm augmentation system of the present invention which performs a particular function. Thus, a "component" may comprise more than one physical part or device. Similarly, a "sub-component" is a conceptual sub-part of a component which performs a particular function. As is the case for a component, a "sub-component" may comprise more than one physical part or device.

"Signaling components" are devices capable of augmenting the analyte monitoring device alert or alarm signal, for example, the GlucoWatch biographer's alert signal, by generating a sensory stimulus, and thereby alerting persons to analyte levels outside of a predetermined range. A "first signaling component" typically serves to alert the user of the monitoring device or someone in close proximity; a "second signaling component" typically serves to alert persons other than the user. In general, signaling components are capable of generating sensory stimuli of at least one of the following types: (i) auditory; (ii) visual; (iii) tactile, including but not limited to kinesthetic; (iv) olfactory; (v) gustatory; and (vi) variations and combinations thereof.

A "transmitter component" is a device capable of communicating an alarm signal to an external communication target, and/or to first and/or second signaling components, when present.

A "processor component" refers to a component capable of integrating alarm signals received from the GlucoWatch biographer and from the other alarm system components, as well as controlling the functioning of the other components.

The term "housing" refers to a structure that physically contains a component or components of the alarm augmentation system of the present invention. The housing may be of any suitable material, including plastic. "Components within a single housing" are those contained within a single structure, as distinguished from "components within several housings" or "components each within individual housings," etc.

"Operably connected" means any kind of telemetric or hard link by which data may be communicated between or among the analyte monitoring device and/or the component(s) of the alarm augmentation system of the present invention.

The terms "wire-like," "cable-like," and "hard link" are terms that refer to tangible connections capable of transmitting data. Transmission may occur electronically or by other methods, e.g., via transmission of light pulses along fiber optic cables. In contrast, the terms "wireless" or "telemetric" intend devices capable of transmitting data without a tangible connection. Examples of telemetric communication methods include electromagnetic waves and infrared radiation, and are further described in the subsection entitled "Intra- and inter-system communication" appearing below.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g., second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female. A "user" or "subject" refers to a person or animal whose analyte levels are being monitored by an analyte monitoring device. Thus, for example, a user or subject of the GlucoWatch biographer, glucose monitoring device is one whose glucose levels are being monitored by that device.

The terms "another" and "others" refer to a person or to persons, respectively, other than a "user" or "subject" as defined above. Further, these terms may refer to an animal that, for example, is trained as an assistance animal (e.g., guide dogs, service dogs, seizure alert dogs, etc.).

The term "emergency personnel" refers to persons such as paramedics, firepersons, policepersons, and others trained to respond to medical emergencies who are available to respond and who may respond upon being summoned.

An "external communication target" is an entity that is the target of data communicated by the transmitter component of the alarm system. Such targets may include, but are not limited to, the following: (1) pagers, for example, pagers carried by a significant other, parent, relative or other care giver, or by the user's physician; (2) computers, such as the computer of the user's physician or of a health-care facility; and (3) phone lines, such as 911 emergency response lines, the phone line of a physician or of a parent, significant other, relative or care-giver. Additional targets may be apparent to persons of ordinary skill in the art, in light of the teachings of the present specification.

The term "transdermal" includes both transdermal and transmucosal techniques, i.e., extraction of a target analyte across skin, e.g., stratum corneum, or mucosal tissue. Aspects of the invention which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890 and 6,023,629 and PCT Publication No. WO 96/00109, published Jan. 4, 1996.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch® (Cygnus, Inc., Redwood City, Calif.) biographer glucose monitor (See, e.g., Tamada, et al. (1999) JAMA 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," or "sensing mechanism," encompasses any device that can be used to measure the concentration or amount of an analyte, or derivative thereof, of interest in a subject. Preferred sensing devices for detecting analytes generally include electrochemical devices, optical and chemical devices and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U.S. Pat. No. 5,747,806).

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some catalytic materials, membranes, and fabrication technologies suitable for the construction of amperometric biosensors are described by Newman, J. D., et al.(1995) Analytical Chemistry 67:4594–4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in WO 97/02811, published Jan. 30, 1997. The ionically conductive material may comprise a biocide. For example, during manufacture of an AutoSensor assembly, one or more biocides may be incorporated into the ionically conductive material. Biocides of interest include, but are not limited to, compounds such as chlorinated hydrocarbons; organometallics; hydrogen releasing compounds; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material which is ionically conductive (e.g., water with ions therein), or alternatively it can be a material, such as a sponge-like material or hydrophilic polymer, used to keep the water in place. Such collection reservoirs can be in the form of a hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising a collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,735,273, 5,827,183, and 6,201,979, all herein incorporated by reference.

The term "gel retaining layer" or "gel retainer" refers to a component of a collection assembly that is substantially planar and typically contacts both the collection insert layer and the electrode assembly.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a mask layer, collection insert layer, a gel retaining layer, an electrode assembly, and a support tray. The AutoSensor assembly may also include liners where the layers are held in approximate, functional relationship to each other. Exemplary collection assemblies and AutoSensor structures are described, for example, in International Publication WO 99/58190, published Nov. 18, 1999; and U.S. Pat. Nos. 5,735,273 and 5,827,183. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it give various cases of the phenomenon represented (McGraw-Hill Dictionary of Scientific and Technical Terms, S. P. Parker, ed., Fifth Edition, McGraw-Hill Inc., 1994). In the context of the GlucoWatch biographer, a parameter is a variable that influences the value of the blood glucose level as calculated by an algorithm.

"Decay" refers to a gradual reduction in the magnitude of a quantity, for example, a current detected using a sensor electrode where the current is correlated to the concentration of a particular analyte and where the detected current gradually reduces but the concentration of the analyte does not.

2. Modes of Carrying Out the Invention

Before describing the present invention in detail, it is to be understood that this invention is not limited to particular combinations or process parameters, as such may, of course, vary. It is also to be understood that the terminology used herein is for the purpose of describing particular embodiments of the invention only, and is not intended to be limiting.

2A. General Overview of the Invention

The present invention relates to a system for augmenting an alert or alarm signal from an analyte monitoring device, in particular, a glucose monitoring device, wherein the improvement comprises an augmented alarm system. Embodiments of the augmented alarm system may comprise at least (a) a first signaling device, for producing an augmented alarm signal and thereby improving the effectiveness of the GlucoWatch biographer in alerting the user. Embodiments may additionally include (b) a transmitter component, for transmitting an augmented alarm signal to external communication targets and to the first signaling component. These individual components are described in further detail below, as are specific embodiments of an enhanced GlucoWatch biographer of the present invention. Modifications of the GlucoWatch biographer are typically, but not necessarily, made to the durable element of the system. In some aspects of the present invention modifications are made to the circuitry of the durable element of the system.

In the enhanced GlucoWatch biographer of the present invention, the first signaling component and the transmitter component are in operative communication with the GlucoWatch biographer and with each other, either by hardware or telemetric device(s). Details of inter- and intra-system communication are described in further detail below.

The present invention further relates to an alarm augmentation system for an analyte monitoring device, wherein the analyte monitoring device comprises an acquisition and a display unit. The alarm augmentation system comprises at least (a) a first signaling component for producing an alarm signal to alert the user of the analyte monitoring device to analyte levels outside of a predetermined range, and/or (b) a transmitter component for transmitting an alarm signal to external communication targets and to the first signaling component, when present. Some embodiments may include both.

Other embodiments may also include (c) a second signaling component, for producing alarm signals to alert a person or persons other than the user of said analyte monitoring device to analyte levels outside of a predetermined range. Further embodiments may additionally comprise (d) a processor component for receiving and integrating information received from both the analyte monitoring device and from the other components of the augmented alarm system, and for controlling the operation of those components. Specific embodiments of the augmented alarm system are described in further detail below.

The components of the augmented alarm system are in operative communication with each other and with the analyte monitoring device; further, the transmitter component, when present, is in operative communication with external communication targets. The specifics of these intra- and inter-system communications are described in further detail below.

2A(i). First Signaling Component and Second Signaling Component

Embodiments of the present invention may include a first signaling component and/or a second signaling component. Preferred embodiments may include at least a first signaling component, and may further include both.

The first signaling component comprises a sensory stimulus generator for generating an augmented alarm signal and thereby improving the effectiveness of the alarm signal generated by the analyte monitoring device (e.g. the alert signal of the GlucoWatch biographer) in alerting a user. Similarly, the second signaling component comprises a sensory stimulus generator for alerting a person or persons other than the user.

Both the first and second signaling components comprise at least one sensory stimulus generator, including but not limited to the following:

1) an aural stimulus generator, which may merely amplify the alarm sound produced by the analyte monitoring device (e.g., the alert signal of the GlucoWatch biographer) or alternately generate sounds different from those produced by the device;

2) a visual stimulus generator, for example, one which turns on or flashes the lights in the room where the user of the GlucoWatch biographer is located, or which independently produces colored or flashing light;

3) a tactile stimulus generator, which, for example, generates pressure, vibration, changes in temperature or mild electrical shocks. Such a tactile stimulus generator may comprise a kinesthetic stimulus generator, which produces movement of the user relative to his/her surroundings. An example would be a vibrator which causes vibration of a chair or bed in which the user is sitting or reclining;

4) an olfactory stimulus generator, which releases various odorant compounds; and 5) a gustatory stimulus generator, which causes the release of salty, sweet, sour or bitter compounds in the mouth, or a combination of those compounds.

Both the first and second signaling components, when present, are in operative communication with the analyte monitoring device, and with the other alarm augmentation system components, either directly and/or via a processor component when such is present.

For example, in embodiments of the analyte monitoring device of the present invention wherein the display unit of that device comprises a first signaling component, that component may be in direct operative communication with the acquisition unit. In embodiments wherein the display unit comprises both a transmitter component and a first signaling component, the first signaling component may be in direct operative communication with both the acquisition device and the transmitter component; alternately, there may be a serial connection from the acquisition unit to the transmitting component to the first signaling component. Communication may be either uni- or bi-directional between these various components.

Similarly, in embodiments comprising a second signaling component in addition to a transmitting component and a first signaling component, the second signaling component may be in operative communication with both the acquisition unit and the first signaling component, directly and/or indirectly, for example, by virtue of a connection from the acquisition unit to the transmitter component, and subsequent parallel connections between the transmitting component and the first and second signaling components.

In general, communication between the signaling component(s) and the analyte monitoring device, as well as among the signaling component(s) and the other alarm augmentation system components, may be mediated either by hardware (e.g., a port and a wire-like connector) or by intangible, telemetric device(s) as described in greater detail in the sub-section entitled "Intra- and Inter-System Communication" appearing below.

Both the first and second signaling components may be responsive to alarm signals generated by the analyte monitoring device via the operative connections just described.

For example, in one embodiment, the first signaling component comprises a sound amplifier which directly detects an audio alert or alarm signal generated by the analyte monitoring device, e.g., via a microphone component. The microphone may further include a filtering subcomponent that limits the range of audio alarm signals detectable by the amplifier's microphone.

Alternately, there may be an intermediate processor component that receives input from the analyte monitoring device, integrates that input, and on the basis of a predetermined hierarchy of response, activates, for example, one, both or neither of a first signaling component and a second signaling component.

The signaling components may also be responsive to user inputs. For example, both the first and second signaling components may further comprise an alarm turn-off mechanism, which provides a way for input from the user or others to indicate that responsive action has been taken. In this regard, the alarm signal of both the first and second signaling components may be graded, and may increase in intensity and/or frequency if not answered. In some embodiments, a processor sub-component may be present that is capable of monitoring whether the user (in the case of the first signaling component) and/or person(s) other than the user (in the case of the second signaling component) has activated the turn-off mechanism, and increasing the alarm frequency and/or intensity if the user/other has failed to do so.

Activity of the signaling component(s) may be simultaneous with the monitoring device's alarm, may occur sequentially, or in any predetermined sequence. Similarly, when both a first and a second component are present, either one or both may be active; when both are active, their activity may be either simultaneous or sequential.

2A(ii). Transmitter Component

Some embodiments of the alarm augmentation system of the present invention comprise a transmitter component for communicating the alarm signal to external communication targets. In some embodiments, the transmitter component may further communicate alarm signals to the first and second signaling components, when such components are present.

The transmitter component is in operative communication with the analyte monitoring device and with the other components of the alarm augmentation system, when such are present, either directly or via an intermediate processor component when present. Modes of communication between the analyte monitoring device and the transmitter component, as well as between the transmitter and other components of the alarm augmentation system of the present invention, are discussed in further detail.

The transmitter component is responsive to alarm signals generated by the analyte monitoring device, via the operative links referred to above, either directly, via a receiver sub-component of the transmitter; alternately, it may be detected initially by another component of the alarm system and subsequently communicated to the transmitter component.

The transmitter component may comprise at least one of a variety of different types of devices, including but not limited to the following: (1) a wire or wire-like connection such as a cable; (2) a modem, (3) a radio transmitter; (4) a microwave transmitter; (5) a sound transmitter (subsonic, sonic, or ultrasonic); and (6) an infrared (IR) transmitter. Other suitable devices may be apparent to persons of ordinary skill in the art, in light of the teachings of the present specification.

In response to an alarm signal, the transmitter component contacts an external communication target (e.g., a first and/or second signaling component). External communication targets may include, but are not limited to, the following: (1) pagers, for example, pagers carried by a significant other, parent, other relative or care giver, or the user's physician; (2) computers, such as the computer of the user's physician or of a health-care facility; and (3) phone lines, such as 911 emergency response lines, the phone line of a physician or of a parent, significant other, relative or caregiver. Additional targets may be apparent to persons of ordinary skill in the art, in light of the teachings of the present specification.

In some embodiments of the invention, the transmitter component may further be capable of receiving input from remote sources, such as a telephone line or computer, and communicating them to the other components of the alarm augmentation system, either directly or via a processor component, when one is present.

Modes of communication between the transmitter component of the alarm augmentation system and external communication targets, and between remote sources of input and the transmitter, are discussed in further detail below.

In another embodiment of the present invention, the alarm augmentation system comprises a transmitting component capable of relaying the initial alarm signal to a second signaling component remote from the analyte monitoring device. Upon receipt of that signal, the second signaling component produces an augmented alarm at the remote location. For example, a relay unit (comprising the transmitting component) may be placed proximal to the acquisition unit. The acquisition unit emits an alert or alarm signal, this signal is communicated (for example, by a wire or wire-like connection such as a cable; a modem, a radio transmitter; a microwave transmitter; a sound transmitter (subsonic, sonic, or ultrasonic); and/or an infrared (IR) transmitter) to the relay unit. The relay unit then communicates the signal to a second, remote, signaling component (which may also include a display unit to show, for example, the analyte amount or concentration or a trend of analyte amount or concentration, e.g., a hyper- or hypo-glycemic trend). Communication with the second signaling component may be via any of the above described modes, as well as via, for example, phone lines, the internet, and/or an intranet. The second signaling component may, for example, be used to alert a doctor, home practitioner, parent, significant other, or medical emergency personnel.

2A(iii). Processor Component

Some embodiments of the alarm augmentation system of the present invention also comprise a processor component, e.g., for evaluating the incoming alarm signal, integrating user inputs, coordinating the alarm augmentation system's response to the alarm signal, and controlling the other alarm system components.

The processor component may comprise a variety of devices, including but not limited to one or more microprocessors.

The processor component is typically responsive to the alarm signal generated by the analyte monitoring device. As discussed above, the GlucoWatch biographer alert signal may be detected by the processor component directly, via a receiver sub-component of the processor, or it may be detected initially by another component of the alarm system and subsequently communicated to the transmitter component. Modes of communication between the GlucoWatch biographer and the processor component, as well as between the processor component and other components of the alarm augmentation system of the present invention, are discussed in further detail below.

Further, the processor component is typically capable of receiving and integrating a variety of inputs in addition to the analyte monitoring device alarm signal, including but not limited to the following: (1) inputs from the other alarm augmentation system components, including user inputs made into those other components; (2) user inputs made directly into the processor component, e.g., via sensitivity controls; and (3) inputs from remote sources, either via the transmitter component or alternately directly via a second receiver sub-component. Other possibilities may be apparent to persons of ordinary skill in the art, in light of the teachings of the present specification.

The processor component may further be capable of controlling the other components of the alarm augmentation system, including but not limited to the following capabilities: (1) determining which of the various components to activate, and the order in which they are activated; and (2) controlling the functioning of the various components, including (a) the frequency and/or intensity of the augmented alarm signals generated by the signaling components; (b) determining whether the transmitter component may communicate with external communication targets, which targets the transmitter component may communicate with, the order in which the communication may occur, and the nature of the communication; (c) determining whether the transmitter component may receive inputs from external sources; and (d) controlling the sensitivity of the system to the analyte monitoring device alarm signal. Other capabilities may be apparent to persons of ordinary skill in the art, in light of the teachings of the present specification.

2A(iv). Intra- and Inter-System Communication

The analyte monitoring device is in operative communication with the alarm augmentation system. Likewise, in embodiments of the alarm augmentation system comprising more than one component, the components are in operative communication with each other. In turn, in embodiments of the invention comprising a transmitter component, the alarm augmentation system is in operative communication with external communication targets, and may further be able to receive input from remote data sources.

With respect to those embodiments that do not possess a processor component, the analyte monitoring device is in direct operative communication with the signaling and/or transmitter components included in specific embodiments. In those embodiments which do include the processor component, the GlucoWatch biographer is in direct operative communication with the processor component, which in turn is in operative communication with the remaining component or components. Alternately, it is also possible for the analyte monitoring device to be in simultaneous communication with the processor component and with the signaling and/or transmitter components.

The operative communication can include, for example, the following: both one-way and bi-directional communication from the analyte monitoring device to the alarm augmentation system, and both one-way and bi-directional communication among the various components of the alarm augmentation system. There may further be both one-way and bi-directional communication among the alarm augmentation system components, and between external communication targets and external data sources, e.g., healthcare providers, 911 emergency services telephone lines, emergency transport services, pagers, computers, etc.

Communication between the acquisition unit (e.g., the analyte monitoring device) and the alarm augmentation system of the present invention, among the system components, between the system and external communication targets, and between external data sources and the system, may be via a wire or cable-like connection and/or via a telemetric connection. Communications between the various components described herein may, for example, be:

1) One-way communication from the analyte monitoring device to the alarm augmentation system and/or among the alarm augmentation system components. The alarm augmentation system can include components for data storage, user inputs, and the ability to upload information to a host computer, i.e., the system can include a processor component, e.g., one or more microprocessor and associated algorithms or protocols, and a transmitter component, e.g., a modem. Alternately, one or more of the individual system components may include a processor sub-component capable of performing those functions.

2) Two-way communications (send and receive) between the analyte monitoring device and the alarm augmentation system, and/or among the alarm components or components, where data storage, user inputs, and upload to a remote computer can be divided in any combination among the monitor device and the components.

3) A mixture of one-way and two-way (i.e., unidirectional and bi-directional) communication among components. For example, communication between the analyte monitoring device, a processor component, and a first signaling component may be bi-directional and communication between the processor component and a transmitter component in operative communication with a second signaling component may be unidirectional.

4) uni- and/or bi-directional communication, with wireless communications link between the analyte monitoring device and the alarm system, and/or among the alarm system components.

5) uni- and/or bi-directional communication, with wired or wireless communications to a remote communication target, e.g., for data upload or automatic reporting to healthcare provider via telephone, Internet, or wireless communications. For example, the alarm system may include a transmitter component, e.g., a bedside receiver/radio transmitter that automatically reports to a patient's personal physician. Alternately, the transmitter component may be a telephonic or wireless modem that performs this function.

Examples of wireless communications technologies include, but are not limited to the following (for example, short range communication, i.e., less than or equal to 3 meters, or longer range):

Low frequency electromagnetic waves (frequency range about 1 Hz–1 Mega Hz);

Medium frequency electromagnetic waves (frequency range about 1 Mega Hz–500 Mega Hz);

High frequency electromagnetic waves (frequency range about 500 Mega Hz–5 Giga Hz);

Capacitance coupling between, for example, a subject's body and the environment/air (frequency range about 1 Hz–1 Mega Hz);

Inductive coupling (i.e., time varying magnetic field; not freely propagating electromagnetic wave);

Close coupled inductive (i.e., inductive but so weak that it works only at very short range). This would likely require bringing the two components (e.g., a display device and sensor electronics) in close proximity whenever the data needs to be displayed.

Brief electrical contact whenever data is needed at the display.

Infrared coupling (using infrared light, e.g., as in low speed communications links to computers and personal digital assistants), and High frequency acoustic energy, as well as, Combinations and modifications of the above.

One embodiment of the alarm augmentation system of the present invention comprises, a glucose monitoring device, a processing component, a first signaling component, a second signaling component, and a transmitter component. Upon detection of abnormal glucose levels or trends, an alarm signal is generated by the glucose monitoring device, which signal is then be communicated to the alarm augmentation system. The alarm signal may initially be communicated to the processor component. The processor component may subsequently communicate with the first signaling component and cause it to generate an augmented alarm signal in order to alert the user. The user may then press a button on the first signaling component, which turns off the augmented alarm signal.

After a time period, which may have either been preset or previously determined by user input, receipt of additional alarm signals from the analyte monitoring device may again cause the processor to communicate with the first signaling component, and again cause it to generate an augmented alarm signal. It may further communicate with the second signaling component and cause it to communicate the alarm signal to a person or persons other than the user. It may further communicate with the transmitter component, which may then communicate the alarm signal to remote targets, e.g., the user's physician, emergency medical personnel, etc.

Alternately, the user may fail to respond to the initial augmented alarm signal. The user's failure to turn off the first signaling component may be communicated to the processor component, which may then communicate to the second signaling component, causing an augmented alarm signal to be generated in order to alert a person or persons other than the user. The processor may also communicate with the transmitter component, which may in turn communicate with remote targets, e.g., the user's physician, emergency personnel, etc.

In a further embodiment, the processor component may additionally be capable of receiving data from the analyte monitoring device, of storing the data, and of communicating the data to the transmitter component. In addition, the processor component may be capable of performing further functions, such as data analysis, to, for example, predict trends based on the data provided by the analyte monitoring device. Further, the transmitter component may be capable of transmitting the data to remote targets, and of uploading the data to remote targets such as a pager device or a computer.

In one embodiment, the wireless connection or link may be established using a technology called Personal Area Network (PAN; WO 96/36134, N. Gershenfeld, et al., published Nov. 14, 1996, herein incorporated by reference). This technology is an example of capacitance coupling involving the use of the human body to carry current, and thus information, from one device to another. These devices have to be either in direct is contact, or in close proximity, to the body. A low frequency carrier is used to transmit the information.

Other examples may be apparent to persons of ordinary skill in the art, in light of the teachings of the present specification.

2A(v). Housings for the Alarm Augmentation System Components

The components of an alarm augmentation system of the present invention may be contained in separate and independent housings. Alternately, the components may be contained within a single housing. In some embodiments, the alarm augmentation system may have a modular character, and be capable of accommodating a variable number of processing, signaling and transmitter components; in such embodiments, each of the components can be housed independently. In all cases, the components may be in operative communication (i.e., operatively connected) with each other as described above.

In one embodiment, both the analyte monitoring device and the components of the alarm augmentation system of the present invention may all be contained in a single housing. In another embodiment, the analyte monitoring device may be in close proximity to the alarm augmentation system, for example, the analyte monitoring device may be a watch-like device and the alarm augmentation system (or components thereof) may be worn as a similar device adjacent to the analyte monitoring device. In yet another embodiment, the alarm augmentation system may be worn on a different part of the body. In a further embodiment, the alarm augmentation system may be remote to the analyte monitoring device, for example, at a fixed location in the home.

The housings may comprise a variety of materials known in the art, including but not limited to the following: a wide variety of plastic polymers; metals and metal alloys; fiberglass; ceramic materials; and composite materials such as plastic polymers impregnated with graphite or silicon nitride fibers.

2B. Exemplary Monitoring Systems and Analytes

2B(i). Exemplary Analyte Monitoring Systems

Numerous analyte monitoring systems can be used in the practice of the present invention. Typically, the analyte monitoring system used to monitor the level of a selected analyte in a target system comprises a sampling device, which provides a sample comprising the analyte, and a sensing device, which detects the amount or concentration of the analyte or a signal associated with the analyte amount or concentration in the sample.

One exemplary analyte monitoring system (the GlucoWatch biographer) is described herein for monitoring glucose levels in a biological system via the transdermal extraction of glucose from the biological system, particularly an animal subject, and then detection of signal corresponding to the amount or concentration of the extracted glucose. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (e.g., a biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing a selected algorithm) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

Figure 1:
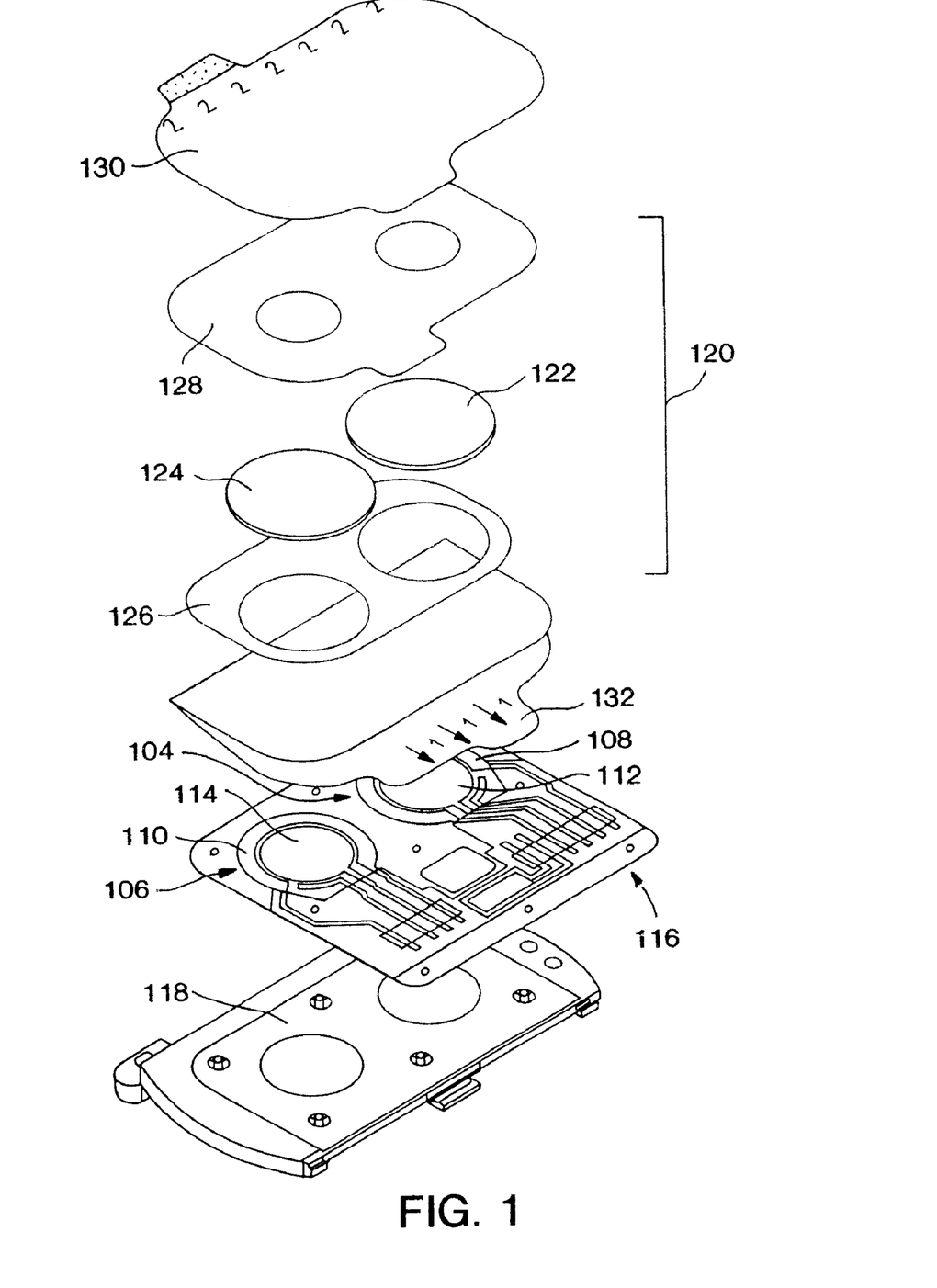
FIG. 1 presents a schematic of an exploded view of exemplary components comprising one embodiment of an AutoSensor for use in an analyte monitoring system.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 1, an exploded view of exemplary components comprising one embodiment of an AutoSensor for use in an iontophoretic sampling system is presented. The AutoSensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In one embodiment, the electrode assemblies include bimodal electrodes. A mask layer 128 (for example, as described in PCT Publication No. WO 97/10356, published Mar. 20, 1997, and U.S. Pat. Nos. 5,735,273, 5,827,183, 6,141,573, and 6,201,979, all herein incorporated by reference) may be present. Other AutoSensor embodiments are described in WO 99/58190, published Nov. 18, 1999, herein incorporated by reference.

The mask and retaining layers are preferably composed of materials that are substantially impermeable to the analyte (e.g., glucose) to be detected (see, for example, U.S. Pat. Nos. 5,735,273, and 5,827,183, both herein incorporated by reference). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 1 (i.e., an exemplary AutoSensor) are intended for use in a automatic sampling system which is configured to be worn like an ordinary wristwatch, as described, for example, in PCT Publication No. WO 96/00110, published Jan. 4, 1996, herein incorporated by reference. The AutoSensor in this case is a consumable element. A durable element, that is the wristwatch housing into which the AutoSensor is inserted, is also provided. The durable element can further include suitable electronics (e.g., one or more microprocessor(s), memory, display and other circuit components) and power sources, for example, for operating the automatic sampling system. The durable element also provides means to provide an audible alert when glucose levels in a subject being monitored are outside of a predetermined range. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc. The durable component of the GlucoWatch biographer provides a variety of electronic configurations (i.e., circuitry) that may be modified to accommodate components of the alarm augmentation system of the present invention. Such modifications include but are not limited to (a) reconfiguring the confidence loop circuitry of the GlucoWatch biographer; (b) modifying the transmission and receipt lines or transmission and receipt line circuitry of the GlucoWatch biographer, and (c) modifying the sweat probe or sweat probe circuitry of the GlucoWatch biographer. Other modifications may be apparent to persons of ordinary skill in the art in light of the teachings of the present invention.

The sensing electrode can be, for example, a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in European Patent Publication 0 942 278 A2, published Sep. 15, 1999, herein incorporated by reference.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594–4599, 1995, herein incorporated by reference).

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

The automatic sampling system can transdermally extract the sample over the course of a selected period of time using reverse iontophoresis. The collection reservoir comprises an ionically conductive medium, preferably the hydrogel medium described hereinabove. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (for example, glucose) within a reservoir is also in contact with the reservoir. Typically, there are two collections reservoirs, each comprising glucose oxidase, and each in operative contact with iontophoretic electrode and a sensing electrode. The iontophoretic electrode may be a bimodal electrode that also serves, non-concurrently, as a counter electrode to the sensing electrode (see, for example, U.S. Pat. No. 5,954,685, herein incorporated by reference).

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT Publication No. WO 96/00110, published Jan. 4, 1996, herein incorporated by reference. Typically, the electrical potential is alternated between two reservoirs to provide extraction of analyte into each reservoir in an alternating fashion (see, for example, U.S. Pat. Nos. 6,023, 629, 5,954,685, both herein incorporated by reference). Analyte is also typically detected in each reservoir.

As an example, to extract glucose, the applied electrical current density on the skin or tissue can be in the range of about 0.01 to about 2 $mA/cm^2$. In order to facilitate the extraction of glucose, electrical energy can be applied to the electrodes, and the polarity of the electrodes can be, for example, alternated so that each electrode is alternately a cathode or an anode. The polarity switching can be manual or automatic. A device and method for sampling of substances using alternating polarity is described in U.S. Pat. No. 5,771,890, issued Jun. 30, 1998, herein incorporated by reference.

When a bimodal electrode is used (e.g., U.S. Pat. No. 5,954,685, issued Sep. 21, 1999, herein incorporated by reference), during the reverse iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (e.g., using a statistical technique or algorithm or combination of techniques) so that the system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,144,869, 6,233,471, 6,180,416, herein incorporated by reference.

In a further aspect of the present invention, the sampling/sensing mechanism and user interface may be found on separate components. Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661, herein incorporated by reference), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841, herein incorporated by reference. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link or connection, i.e. provided by a "virtual cable," for example, a telemetry link. This wireless link can be uni- or bi-directional between the two components. In the case of more than two components, links can be a combination of wire-like and wireless.

2B(ii). Exemplary Analytes

The analyte can be any one or more specific substance, component, or combinations thereof that one is desirous of detecting and/or measuring in a chemical, physical, enzymatic, or optical analysis.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme AND-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytoin), chemotherapy (e.g., adriamycin), hyperactivity (e.g., ritalin), and anti-organ-rejection (e.g., cyclosporin).

Preferably, a sensor electrode is able to detect the analyte that has been extracted into the one or more collection reservoirs when present at nominal concentration levels. Suitable exemplary biosensor electrodes and associated sampling systems as described in are described in PCT Publication Nos. WO 97/10499, published Mar. 20, 1997 and WO 98/42252, published Oct. 1, 1998, both herein incorporated by reference herein.

A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl). The glucose is detected, e.g., using glucose oxidase and detecting the hydrogen peroxide reaction product.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea.

2C. Exemplary Embodiments of the Alarm Augmentation System

The alarm augmentation system of the present invention may exist as a singe unit device, or alternatively, may comprise multiple units.

2C(i). Single Unit Devices

The augmented alarm system may exist as a single unit device combined with an analyte monitoring device.

In an exemplary device, the alarm augmentation system is incorporated into a durable element of the analyte monitoring device. In one embodiment of this exemplary device, an aspect of the durable element of the GlucoWatch biographer circuitry is modified to provide an augmented alarm signal, which may be (i) auditory, (ii) visual, (iii) tactile, including but not limited to kinesthetic, (iv) olfactory, (v) gustatory, and also be (vi) variations and combinations thereof. Other types of signals, sensory or otherwise, are also possible. For example, the iontophoretic channels (or leads) of the durable component of GlucoWatch biographer are modified so as to be capable of delivering an electrical current to provide a tactile stimulus to the user. Corresponding modifications to the consumable element of the GlucoWatch biographer may be made as well, for example, increasing the size or surface area of the hydrogels in order to provide a suitable stimulus to the user. Further, the consumable component of the GlucoWatch biographer (i.e., an AutoSensor, or similar structures in other analyte monitoring devices) may be modified to include components of an alarm augmentation system, for example, including a speaker device capable of providing an amplified signal in the AutoSensor assembly. Exemplary AutoSensor assemblies are described, for example, in WO 99/58190, published Nov. 18, 1999, herein incorporated by reference in its entirety. Other modifications are also possible, and may be apparent to persons of ordinary skill in the art in light of the teachings of the present specification.

In the case of an augmented alarm system and an analyte monitoring device within a single housing, the analyte monitoring device typically comprises an acquisition unit and a display unit, which are contained within a single housing. The display unit may further comprise a first signaling component; in some embodiments, the first signaling component may be an aural stimulus generator. Preferably, the display unit may further comprise a volume control for varying the intensity of the aural alarm signal.

Other embodiments may be apparent to persons of ordinary skill in the art in light of the teachings of the present specification.

2C(ii). Multiple Unit Systems

Some embodiments of the augmented alarm system of the present invention may have a modular character, and be capable of accommodating a variable number of processing, signaling and transmitter components. In such embodiments, at least one of the components may be housed independently of the acquisition unit (e.g., an analyte monitoring device) and/or of other components comprising the alarm augmentation system. In all cases, the components may be in operative communication with each other as described above.

Multiple-unit alarm augmentation systems for use with an enhanced GlucoWatch biographer include but are not limited to the following examples. In some exemplary embodiments, the enhanced GlucoWatch biographer may comprise a transmitter component, wherein the transmitter itself may comprise a port that provides a connection to a first signaling component of an alarm augmentation system. The first signaling component of this exemplary embodiment may comprise an auditory stimulus generator, and preferably one with a volume control.

The port may comprise a serial port that is added to the GlucoWatch biographer, being placed in operative connection therewith, and a wire-like or cable-like connector for connecting the GlucoWatch biographer and a first signaling component. Alternately, the port may comprise a modification to some aspect of the GlucoWatch biographer's circuitry. Such modifications include but are not limited to (a) reconfiguring the confidence loop circuitry of the GlucoWatch biographer; (b) modifying the transmission and receipt lines or transmission and receipt line circuitry of the GlucoWatch biographer, and (c) modifying the sweat probe or sweat probe circuitry of the GlucoWatch biographer. Other modifications may be apparent to persons of ordinary skill in the art in light of the teachings of the present invention.

Multiple-unit versions of the augmented alarm system for an analyte monitoring device include but are not limited to the following. Common to the embodiments of this aspect of the invention is an analyte monitoring device that comprises an analyte monitoring unit and a display unit. Such units (or components) of an analyte monitoring device may be contained within a single housing; or in another aspect, they are contained in different housings, and operably connected by either hardware or telemetric device(s), preferably telemetric. The GlucoWatch biographer is an example of an analyte monitoring device where the sampling device, sensing device, microprocessors, controls, and display are combined into a single unit to worn like a wrist watch. Examples of multi-component analyte monitoring devices are provided in WO 00/47109, published Aug. 17, 2000, herein incorporated by reference in its entirety. In one exemplary embodiment, the acquisition unit is worn by the user, and the display unit is separable, so that it may be placed, for example, at a different physical location on the user, on a night stand, or a desk, etc. Such a display unit may comprise at least either (a) a transmitting component or (b) a first signaling component. More preferred embodiments may include both.

In an exemplary embodiment, the acquisition unit, the display unit and the transmitting component may all be contained within a single housing, while the first signaling component may be contained in an independent housing. The user may therefore place the first signaling component in a location that maximizes the effectiveness of the alarm signal in alerting him or her to the existence of abnormal analyte levels. For example, in cases where the first signaling component generates a sound alarm signal, it may be placed on a night stand nearer to the user's ears.

In another exemplary embodiment, the acquisition unit, the display unit and the transmitting component may all be contained within a single housing while both the first signaling component and the second signaling component may each be contained within separate independent housings. Thus, it is possible to place the second signaling component in a location remote from the user where it can alert a person or person(s) other than the user (e.g., a significant other, parent, other family member, or caretaker) to the existence of abnormal analyte levels.

In still another alternate embodiment, the augmented alarm system may further comprise a processor component. In one example of these embodiments, the processor component may be contained within a single housing along with the acquisition unit, the display unit and the transmitter component, while the first and second signaling components may be housed separately, as described above.

As is apparent to one of skill in the art, various modification and variations of the above embodiments can be made without departing from the spirit and scope of this invention. Such modifications and variations are within the scope of this invention.

What is claimed is:

1. An improved glucose monitoring device, comprising a durable element comprising (A) a housing to which a consumable element can be operably connected, (B) circuitry, (C) a display element, (D) one or more microprocessor elements, (B) electrical connector elements, and (F) means to provide an audible alert when glucose levels in a subject being monitored are outside of a predetermined range, wherein (a) said consumable element comprises a mask layer, a collection insert layer comprising two hydrogels, a gel retaining layer, an electrode assembly comprising two iontophoretic electrodes and two sensing electrodes, and a support tray, and (b) the improvement comprises modification of the circuitry of the durable element of said device to provide an augmented alarm signal capable of alerting a user of said device to glucose levels outside of a predetermined range, said alarm signal selected from the group consisting of (i) tactile stimulus, (ii) auditory stimulus, (iii) visual stimulus, and (iv) variations and combinations thereof.

2. The improved glucose monitoring device of claim 1, wherein said device comprises iontophoretic channels, and said iontophoretic channels are modified to be capable of delivering an electrical current to provide a tactile stimulus.

3. The improved glucose monitoring device of claim 1, further comprising said durable element operably linked to the consumable element.

4. An improved glucose monitoring device, comprising a durable element comprising (A) a housing to which a consumable element can be operably connected, (B) circuitry, (C) a display element, (D) one or more microprocessor elements, (E) electrical connector elements, and (F) means to provide an audible alert when glucose levels in a subject being monitored are outside of a predetermined range, wherein (a) said consumable element comprises a mask layer, a collection insert layer comprising two hydrogels, a gel retaining layer, an electrode assembly comprising two iontophoretic electrodes and two sensing electrodes, and a support tray, and (b) the improvement comprises modification of the circuitry of the durable element of said device to provide a connection to a first signaling component for producing alarm signals capable of alerting a user of said device to glucose levels outside of the predetermined range.

5. The improved glucose monitoring device of claim 4, wherein said first signaling component is selected from the group consisting of (i) an auditory stimulus generator; (ii) a visual stimulus generator; (iii) a tactile stimulus generator; (iv) an olfactory stimulus generator; and (v) variations and combinations thereof.

6. The improved glucose monitoring device of claim 4, wherein the connection is via a telemetering system, wherein said telemetering system is selected from the group consisting of (i) electromagnetic radiation; (ii) capacitance coupling; (iii) inductive coupling (iv) infrared coupling; and (v) variations and combinations thereof.

7. The improved glucose monitoring device of claim 4, wherein the connection is via a wire-like connector.

8. The improved glucose monitoring device of claim 4, further comprising said durable element operably linked to said consumable element.

9. The improved glucose monitoring device of claim 4, wherein said modification comprises adding a serial port to said glucose monitoring device, said port being in operative communication with said glucose monitoring device and providing said connection.

10. The improved glucose monitoring device of claim 4, wherein said glucose monitoring device comprises transmission and receipt lines, and said modification comprises modifying the transmission and receipt lines of said glucose monitoring device to provide said connection.

11. An alarm augmentation system for an analyte monitoring device, comprising
   an analyte monitoring device, said analyte monitoring device comprising
      an acquisition unit comprising, a durable element comprising (A) a housing to which a consumable element can be operably connected, (B) circuitry, (C) one or more microprocessor elements, and (D) electrical connector elements, wherein (a) said consumable element comprises a mask layer, a collection insert layer comprising two hydrogels, a gel retaining layer, an electrode assembly comprising two iontophoretic electrodes and two sensing electrodes, and a support tray; and
      a display unit, operably linked to said acquisition unit, wherein (i) said display unit comprises means to provide an audible alert when an analyte level, in a subject being monitored, is outside of a predetermined range, and (ii) said acquisition unit and said display units are separately housed; and
   an alarm augmentation system comprising a first signaling component, capable of producing alarm signals to alert a subject in response to analyte levels outside of a predetermined range, said first signaling component operably linked to said display unit.

12. The alarm augmentation system of claim 11, further comprising a transmitter component, operably linked to said display unit, said transmitter component capable of transmitting alarm signals to at least one external communication target.

13. The alarm augmentation system of claim 12, wherein said transmitter further provides an operative link between said display unit and said first signaling component.

14. The alarm augmentation system of claim 12, wherein said transmitter component comprises a serial port and a wire-like connector, said port and said connector capable of connecting with at least one external communication target.

15. The alarm augmentation system of claim 12, wherein said transmitter component comprises a telemetering system selected from the group consisting of (i) electromagnetic radiation; (ii) capacitance coupling; (iii) inductive coupling; (iv) infrared coupling; and (v) combinations and variations thereof.

16. The alarm augmentation system of claim 15, wherein said telemetering system is capable of connecting with said first signaling component and said external communication target.

17. The alarm augmentation system of claim 15, wherein (a) said external communication target is a second signaling component, capable of producing alarm signals to alert a person or persons other than the user of said analyte monitoring device to analyte levels outside of the predetermined range, (b) said second signaling component is selected from the group consisting of (i) an auditory stimulus generator; (ii) a visual stimulus generator; (iii) a tactile stimulus generator; (iv) an olfactory stimulus generator; (v) a gustatory stimulus generator; and (vi) variations and combinations thereof, and (c) said second signaling component is operably linked to said transmitter component via said telemetering system.

18. The alarm augmentation system of claim 17, further comprising
   a processor component, wherein said processor component is (i) operably linked to said display unit, said acquisition unit, said transmitter component, and said first and second signaling components, (ii) capable of receiving and processing information received from said display unit, said acquisition unit, and said first and second signaling components, and (iii) capable of controlling the operation of said transmitter component and said first and second signaling components.

19. The alarm augmentation system of claim 11, wherein said first signaling component comprises an auditory stimulus generator, and said auditory stimulus generator provides a volume control for varying the volume of auditory stimuli generated thereby.

20. The alarm augmentation system of claim 11, wherein said first signaling component is selected from the group consisting of (i) an auditory stimulus generator; (ii) a visual stimulus generator; (iii) a tactile stimulus generator; (iv) an olfactory stimulus generator; (v) a gustatory stimulus generator; and (vi) variations and combinations thereof.

* * * * *

UNITED STATES PATENT AND TRADEMARK OFFICE
CERTIFICATE OF CORRECTION

PATENT NO.    : 6,553,244 B2
DATED         : April 22, 2003
INVENTOR(S)   : Matthew J. Lesho et al.

It is certified that error appears in the above-identified patent and that said Letters Patent is hereby corrected as shown below:

<u>Column 28,</u>
Line 27, "elements, (B) electrical connector" should be -- elements (E) electrical connector --.

Signed and Sealed this

Nineteenth Day of August, 2003

JAMES E. ROGAN
*Director of the United States Patent and Trademark Office*